United States Patent [19]

Stojkovic et al.

[11] Patent Number: 4,606,919

[45] Date of Patent: Aug. 19, 1986

[54] VACCINE FOR THE TREATMENT OF URINARY TRACT INFECTIONS CONTAINING ALUMINUM PHOSPHATE

[75] Inventors: Llubinko Stojkovic; Rodmila Pavic, both of Basel; Vera Spasojevic, Augst, all of Switzerland

[73] Assignee: Solco Basel AG, Basel, Switzerland

[21] Appl. No.: 772,130

[22] Filed: Aug. 30, 1985

[30] Foreign Application Priority Data

Aug. 31, 1984 [CH] Switzerland .......................... 4181/84

[51] Int. Cl.⁴ ............................................. A61K 39/02
[52] U.S. Cl. ........................................ 424/92; 424/88; 424/93; 435/253; 435/261; 435/849; 435/852; 435/873; 435/885
[58] Field of Search ............................. 424/92, 88, 93; 435/253, 261, 849, 852, 873, 885

[56] References Cited

U.S. PATENT DOCUMENTS

| | | | |
|---|---|---|---|
| 3,183,161 | 5/1965 | McLean, Jr. et al. | 424/89 |
| 3,501,770 | 3/1970 | Gale et al. | 424/92 X |
| 3,608,066 | 9/1971 | Illartein | 424/92 X |
| 4,298,597 | 11/1981 | Acres et al. | 424/92 |
| 4,338,298 | 7/1982 | Myers | 424/92 |

FOREIGN PATENT DOCUMENTS 2397839  7/1977  France .

Primary Examiner—Howard E. Schain
Attorney, Agent, or Firm—Ladas & Parry

[57] ABSTRACT

A vaccine for curative and prophylactic treatment of urinary tract infections in humans. The vaccine contains inactivated bacteria which originate from the cultures of 8 to 14 uropathogenic bacteria strains isolated from the urine of a person suffering from a urinary tract infection and aluminum phosphate in an amount of 1.5–10 mg of AlPO$_4$ per ml of solution. Such bacteria are of the species *E. coli, Klebsiella pneumoniae, Proteus mirabilis, Proteus morganii* and *Streptococcus faecolis*.

12 Claims, No Drawings

VACCINE FOR THE TREATMENT OF URINARY TRACT INFECTIONS CONTAINING ALUMINUM PHOSPHATE

Vaccines against various diseases in humans or animals have already been proposed, and these have also been used for a long time. For example, according to Swiss Pat. No. 158,980, an individual mixed vaccine can be prepared for a sick person by removing the germs present on the particular disease focus, for example the tonsils, the vagina, the sputum or the feces, culturing them indiscriminately and inactivating them. According to French Pat. No. 2,034,743, an antigen of the most diverse origins can be rendered water-insoluble by adding aluminium tannate to an appropriate liquid extract; the product has a delayed absorption and hence an extended action.

According to European Pat. No. 28,172, U.S. Pat. No. 4,338,298 or Unlisted Drugs 30 (1978), 123—Gletvax K88, a vaccine based on enteropathogenic strains of the species *Escherichia coli* is said to be used for passive immunization of new-born animals for slaughter. The vaccine is administered intramuscularly or subcutaneously to the dam some time before delivery and protects the calves, piglets and the like, after birth, from diarrhea caused by coli bacteria.

Vaccines based on coli bacteria have also already been proposed for humans. According to German Offenlegungsschrift No. 1,931,195, microorganisms are taken from the sputum of persons suffering from infections of the respiratory tract and are killed and worked up to a vaccine in the form of an aerosol; they are administered by inhalation and are intended for immunotherapy of the respiratory tract. Besides many other species and strains of bacteria, the vaccine contains those of *Escherichia coli*.

According to French Pat. No. 2,397,839, another vaccine consists of dead or attenuated germs of a number of species of bacteria, together with eleven different strains of *Escherichia coli;* it is administered perorally and is to be used for immunization of the gastrointestinal tract and, above all, to cure or protect from gastroenteritis. The vaccine also contains methionine, iron salts, vitamins, Lactobacilli etc.

In contrast, no vaccine has yet been developed which has been specifically directed against infections of the urinary tract and composed on the basis of, in particular, *Escherichia coli*. The absence of such a vaccine is all the more astonishing, since these infections are an important problem in medicine—on the one hand because of their frequent occurrence, which is not becoming less frequent in spite of wide use of antibiotics and chemotherapeutics, and on the other hand because of their tendency towards recurrences (recurrence in over 80% of the cases) and towards a chronic course.

The reason for the previous absence evidently lies in the enormous number of sero types of *Escherichia coli*. In particular, these bacteria have a very complex antigenic structure, with three main groups of antigen: about 160 O antigen types, more than 60 K types and more than 60 H types are known today; combination of these gives about 10,000 serologically different *Escherichia coli* strains. With such a number of strains, it must have appeared hopeless from the beginning to be able to achieve a vaccine which is generally effective against urinary tract infections from a reasonably acceptable number of *Escherichia coli* strains.

To be worthy of a claim for general activity against urinary tract infections at all, such a vaccine would in fact have to guarantee immunity towards cystitis, prostatitis, pyelitis and pyelonephritis, whatever the bacterial origin of the disease. However, it is clear that the wider the range of immunity, the greater the possibility of an immune reaction spreading to endogenous systems.

As is known, the coli bacteria carry fimbriae (pili, fibrillae), which are responsible for adhesion of the coli bacteria of the intestine to the intestinal mucous membrane; without the cooperation of the fimbriae, the coli bacteria would be flushed off the intestine and thus the physiological equilibrium between the coli species and the other bacteria species in the intestine would be severely disturbed. It could therefore be feared that with a vaccine based on coli bacteria, the antibodies produced in the body would react with all the systems which usually carry fimbriae, and thus also with the coli bacteria of the intestine; the consequence would be the abovementioned far-reaching disturbance of the intestinal flora.

Surprisingly, it has now proved to be possible, however, to prepare from a modest number of *Escherichia coli* strains and a few other species of bacteria, which have been isolated from the urine of a person suffering from a urinary tract infection, a vaccine which is specifically and generally active against such infections, but which, in contrast to the previous fears, has virtually no harmful effects on the intestinal flora.

According to the invention, the new vaccine consists of a suspension in sterile isotonic solution, which contains (1) inactivated bacteria which originate from cultures of 8 to 14 uropathogenic bacteria strains isolated from the urine of a person suffering from an infection of the urinary tract, of the species: *Escherichia coli, Klebsiella pneumoniae, Proteus mirabilis, Proteus morganii* and *Streptococcus faecalis,* and are present in an amount of about 50 million to 500 million germs of each strain per ml, one half to three quarters of the strains used belonging to the *Escherichia coli* species, and (2) aluminum phosphate in colloidal form in an amount of 1.5 to 10 mg of $AlPO_4$ per ml.

The vaccine is prepared by culturing, by themselves on a suitable nutrient medium, each of the abovementioned 8 to 14 uropathogenic bacteria strains which have been isolated from the urine of a person suffering from an infection of the urinary tract and of which half to three quarters belong to the species *Escherichia coli,* and, when culturing is concluded, removing the particular biological material formed and inactivating it by known methods, mixing amounts of the inactivated bacteria obtained from the individual strains with one another and diluting the mixture with an amount of a sterile isotonic solution such that about 50 million to 500 million germs of each strain are present per ml, and adding aluminum phosphate in colloidal form up to a concentration of 1.5 to 10 mg of $AlPO_4$ per ml.

The invention is described in detail below.

Urine samples (mid-stream urine) were first isolated from persons suffering from a urinary tract infection and inoculated immediately onto a MacConkey agar; after the inoculation, the agar plates were incubated at 37° C. for 16 to 18 hours and the colonies formed were then isolated and identified by determination of their biochemical and biological properties.

Identification of *Streptococcus faecalis* (Enterococcus)

By Gram staining of characteristic small colonies and the following tests:

| | |
|---|---|
| catalase (in the presence of heated blood) | + |
| hemolysis | −/β |
| growth at 45° C. | + |
| growth at pH 9.6 | + |
| growth in 6.5% NaCl solution | + |
| growth on 40% bile | + |
| detection of polysaccharide antigen D | + |

The following criteria were used to identify the strains of *E.coli*, Proteus and Klebsiella:

| | E. coli | Proteus morganii | Proteus miribilis | Klebsiella pneumoniae |
|---|---|---|---|---|
| Motility | + | + | + | + |
| Growth in KCN medium | − | + | + | − |
| Citrate as C source | − | − | + | + |
| Carbohydrate gas from glucose | + | + | + | + |
| Acid from lactose | + | − | − | + |
| from sucrose | +(d) | − | + | + |
| from maltose | + | − | − | + |
| from mannitol | + | − | − | + |
| from trehalose | + | +(d) | + | + |
| from xylose | +(d) | − | − | + |
| Gelatin hydrolysis | − | − | + | − |
| Indole | + | + | − | − |
| Urease | − | + | + | + |
| H₂S from TSI (triple sugar iron agar) | − | − | + | − |
| Lysine dehydro-carboxylase | + | − | − | + |

The colonies identified in this manner were allowed to grow further on agar plates at 37° C. for 24 hours and were then suspended in physiological saline solution, tested for purity by means of Gram staining and freeze-dried. The individual strains obtained were characterized as follows and labeled as can be seen from the tables.

| Carbo-hydrate | Fermentation of the carbohydrates | | | | | |
|---|---|---|---|---|---|---|
| | *Escherichia coli* strain | | | | | |
| | 455 UB | 525 UB | 560 UB | 616 UB | 654 UB | 719 UB |
| Lactose | + | + | + | + | + | + |
| Sucrose | 0 | 0 | 0 | + | + | + |
| Mannitol | + | + | + | + | + | + |
| Maltose | + | + | + | + | + | + |
| Melibiose | + | + | + | + | + | + |
| Raffinose | 0 | 0 | 0 | 0 | 0 | 0 |
| Rhamnose | + | ± | + | + | + | + |
| Trehalose | + | + | + | + | + | + |
| Salicin | 0 | 0 | 0 | 0 | 0 | + |
| Ribose | + | + | + | + | + | + |
| Amygdalin | 0 | 0 | 0 | 0 | 0 | 0 |
| Galactose | + | + | + | + | + | + |
| Sorbitol | + | + | + | + | + | + |
| Arabinose | + | + | + | + | + | + |
| Glucose | + | + | + | + | + | + |
| Mannose | + | + | + | + | + | + |
| Fructose | + | + | + | + | + | + |
| Adonitol (Ribitol) | 0 | 0 | 0 | 0 | 0 | 0 |
| Inositol | 0 | 0 | 0 | 0 | 0 | 0 |
| Dulcitol | 0 | 0 | 0 | 0 | 0 | 0 |
| Cellobiose | 0 | 0 | 0 | 0 | 0 | + |
| Xylose | + | ± | + | + | + | + |

+ = Acid

| Test | Biochemical properties | | | | | |
|---|---|---|---|---|---|---|
| | *Escherichia coli* strain | | | | | |
| | 455 UB | 525 UB | 560 UB | 616 UB | 654 UB | 719 UB |
| Urea | 0 | 0 | 0 | 0 | 0 | 0 |
| Hemolysis on blood agar plates | 0 | 0 | 0 | 0 | 0 | + |
| Gelatin hydrolysis | 0 | 0 | 0 | 0 | 0 | 0 |
| Citrate | 0 | 0 | 0 | 0 | 0 | 0 |
| Indole | + | + | + | + | + | + |
| H₂S | 0 | 0 | 0 | 0 | 0 | 0 |
| Motility | + | + | + | + | + | + |

+ = positive in 24 hours
0 = negative after 72 hours

| Carbo-hydrate | Fermentation of the carbohydrates | | |
|---|---|---|---|
| | *Klebsiella pneumoniae* K1 16 B | *Proteus mirabilis* 63 B | *Proteus morganii* 58 B |
| Lactose | 0 | 0 | 0 |
| Sucrose | + | 0 | 0 |
| Mannitol | + | 0 | 0 |
| Maltose | + | 0 | 0 |
| Melibiose | 0 | 0 | 0 |
| Raffinose | 0 | 0 | 0 |
| Rhamnose | + | 0 | 0 |
| Trehalose | + | + | 0 |
| Salicin | + | 0 | 0 |
| Ribose | + | + | + |
| Amygdalin | 0 | 0 | 0 |
| Galactose | + | + | + |
| Sorbitol | + | 0 | 0 |
| Arabinose | + | 0 | 0 |
| Glucose | + | + | + |
| Mannose | + | 0 | + |
| Fructose | + | 0 | + |
| Adonitol (Ribitol) | 0 | 0 | 0 |
| Inositol | 0 | 0 | 0 |
| Dulcitol | 0 | 0 | 0 |
| Cellobiose | + | 0 | 0 |
| Xylose | + | + | 0 |

+ = Acid

| Test | Biochemical properties | | |
|---|---|---|---|
| | *Klebsiella pneumoniae* K1 16 B | *Proteus mirabilis* 63 B | *Proteus morganii* 58 B |
| Urea | 0 | + | + |
| Hemolysis on blood agar plates | 0 | 0 | + |
| Gelatin hydrolysis | 0 | + | 0 |
| Citrate | + | + | 0 |
| Indole | 0 | 0 | + |
| H₂S | 0 | + | 0 |
| Motility | 0 | + | + |

+ = positive in 24 hours
0 = negative after 72 hours

| Fermentation of the carbohydrates | |
| --- | --- |
| Carbohydrate | Streptococcus faecalis 676 |
| Lactose | + |
| Sucrose | + |
| Mannitol | + |
| Maltose | + |
| Melibiose | 0 |
| Raffinose | 0 |
| Rhamnose | + |
| Trehalose | + |
| Salicin | + |
| Ribose | + |
| Amygdalin | + |
| Galactose | + |
| Sorbitol | + |
| Arabinose | 0 |
| Glucose | + |
| Mannose | + |
| Fructose | + |
| Adonitol (Ribitol) | 0 |
| Inositol | 0 |
| Dulcitol | 0 |
| Cellobiose | + |
| Xylose | 0 |

+ = Acid

| Biochemical properties | |
| --- | --- |
| Test | Streptococcus faecalis 676 |
| Biochemical properties | |
| Urea | 0 |
| Hemolysis type | not hemolytic |
| Gelatin hydrolysis | 0 |
| Reduction of litmus milk | + |
| Indole | 0 |
| Aesculin | + |
| Growth on a nutrient medium | |
| 40% strength bile | + |
| 6.5% strength sodium chloride | + |
| pH 9.6 | + |
| Temperature resistance | |
| 60° C. for 30 minutes | + |

+ = positive
0 = negative

The morphological properties of the isolated strains described above can be summarized as follows.

Escherichia coli

Gram-negative rods, 1.1–1.5×2.0–6.0 μm (living form), motile by peritrichal flagellae.

Proteus mirabilis and P. morganii

Gram-negative rods, 0.4–0.6×0.1–3.0 μm without capsule, motile by peritrichal flagellae (not all)

Klebsiella pneumoniae

Gram-negative, non-motile rods, 0.3–1.5 μm×0.6–6.0 μm

Streptococcus faecalis

Gram-negative ovoid cocci, 0.5–1.0 μm, non-motile.

The Escherichia coli strains were furthermore investigated for their serological nature, and for this purpose were first subjected to the agglutination test with the polyvalent OK sera A, B, C, D and E on a slide. Further serotyping (determination of the O, K and H antigens) was carried out in accordance with the instructions of Difco Laboratories, Detroit (MI, USA), 1976. This identification gave the following picture:

| Strain | Designation | Sero type |
| --- | --- | --- |
| Escherichia coli | Ec 455 UB | 0 6:K 13:H 1 |
| Escherichia coli | Ec 525 UB | 0 1:K 1:H 7 |
| Escherichia coli | Ec 560 UB | 0 4:K 3:H 5 |
| Escherichia coli | Ec 616 UB | 0 75:—:H 5 |
| Escherichia coli | Ec 654 UB | R - Form |
| Escherichia coli | Ec 719 UB | Hemolytic, cannot be typed |

The 10 strains mentioned and defined above were deposited on Aug. 8, 1984 at the Centraalbureau voor Schimmelcultures, Oosterstraat 1, 3740 AG Baarn (Holland) under the designations CBS 516.84 to CBS 525.84, and were transferred on Dec. 5, 1984 to the Deutsche Sammlung von Mikroorganismen, Grisebachstrasse 8, 3400 Göttingen (Federal Republic of Germany) under the receipt numbers DSM 3229 to DSM 3238.

To prepare the vaccines, the strains were cultured individually on a solid or liquid nutrient medium; a solid nutrient medium is preferably used, for example nutrient agar (Nutrient Agar Difco), which has the following composition:

| meat extract (Difco beef extract) | 3 g/l |
| --- | --- |
| Bacto-Peptone | 5 g/l |
| Sodium chloride | 5 g/l |
| Bacto-Agar | 15 g/l |

The medium is sterilized at 121° C. for 15 minutes; it has a pH of about 7.2.

Roux bottles are used for large-scale preparation, and Petri dishes are used for preparation in the laboratory. Inoculation is carried out with inoculum material, a few ml of which are uniformly distributed over the entire surface. The Roux bottles are closed with cottonwool plugs and the medium is stored with the inoculated surface at the bottom. The inoculated cultures are incubated at 37° C. for 24 hours.

The bacterial lawns are rinsed off with the required amount (depending on the density of growth of the culture in the vessel) of phosphate buffer/saline solution (PBS) with gentle swirling, without damaging the agar surface.

A smear is obtained from each bottle or each Petri dish, stained by the Gram method and tested for purity. Bottles or Petri dishes which appear to be contaminated are discarded. Suspensions which originate from one strain and one harvest are poured together through a sterile nylon gauze.

Inactivation, like the culture itself, takes place individually for each strain. It can be carried out by heating at a temperature of about 55° to 60° C. for about one hour, by treatment with formaldehyde solution or by irradiation with γ-rays. Because of its simplicity, inactivation by heating is preferred.

The amounts obtained by culture are combined and inactivated in a waterbath at 60° C. for one hour, and, after the inactivation with heat, phenol is added (final concentration 0.35%).

A sample of the suspension is taken for the sterility test and for the test for identity, and the concentrated stock amount is stored in a refrigerator.

If the sterility tests show no impurities after 3 days, the preparation process is continued. The sterility test is observed for 14 days, and if the sterility sample shows growth of any organisms, this harvest is eliminated.

The contents of the stock container (inactivated suspensions originating from one strain) are centrifuged at 3,000 rpm for 1 hour in a cooled centrifuge (Sorvall 4 CR, upswing rotor 2,000), the supernatant liquid is removed and the bacterial sediment is suspended in saline solution containing 0.01% of thiomersal. The density of the stock concentrates is determined with a turbidity standard, and the suspension is labeled and stored at 4° C. ($\pm 2°$ C.).

The concentrated suspensions of the 10 strains of *E. coli, Proteus mirabilis, Proteus morganii, Klebsiella pneumoniae* and *Streptococcus faecalis* are mixed so that 1 milliliter of mixture contains:

| | |
|---|---|
| *E. coli*, 6 strains $2.5 \times 10^8$ of each, in total | $1.5 \times 10^9$ germs |
| *Proteus mirabilis*, 1 strain | $7.5 \times 10^7$ germs |
| *Proteus morganii*, 1 strain | $7.5 \times 10^7$ germs |
| *Klebsiella pneumoniae*, 1 strain | $3 \times 10^8$ germs |
| *Streptococcus faecalis*, 1 strain | $5 \times 10^7$ germs |
| Total | $2 \times 10^9$ germs/ml |

The final concentration is obtained by mixing the individual stock suspensions together. The concentration described is achieved by dilution with 0.15M phosphate-buffered salt solution containing 0.01% of Merthiolate (thiomersal). The stock is now kept at room temperature for 24 hours and then stored at 4° C. ($\pm 2°$ C.).

Since aluminum phosphate gel is added, the concentration must be correspondingly higher. The aluminum phosphate gel is prepared as follows:

854 g of potassium aluminum sulfate.12 $H_2O$ are dissolved in 6 liters of water and the solution is filtered. 685 g of trisodium phosphate.12 $H_2O$ are also dissolved in 6 liters of water. The aluminum solution is kept at a temperature of 37° C., since it is readily supersaturated at room temperature. Both solutions are simultaneously poured into 21 liters of water. The precipitate is centrifuged, the sediment is resuspended in 13 liters of water and the suspension is centrifuged again.

Finally, the sediment is resuspended and the suspension is brought to a total volume of 8.1 liters, brought to pH 6.0 with 5N NaOH and autoclaved at 121° C. for one hour. This amount is sufficient to prepare 66 liters of a vaccine containing 3 mg of $AlPO_4$/ml or 0.66 mg of Al/ml.

After testing of the pH, which must be between 6.2 and 7.0, the adsorbed final vaccine is introduced in an amount of 0.5 ml per dose into sterile pyrogen-free ampules with a capacity of 1 ml. It must be ensured that the vaccine is shaken during the introduction.

The total number of inactivated microorganisms in one dose—i.e. 0.5 ml—is about $1 \times 10^9$.

Finally, the vaccine is tested for sterility in accordance with European Pharmacopoeia (2nd edition, 1st supplement 1980), for toxicity in accordance with the specifications of the World Health Organization (weight increase in mice), and for abnormal toxicity in accordance with the European Pharmacopoeia.

The vaccine can also be presented in lyophilized form instead of in the liquid form described above. It is prepared as described below.

The concentrated inactivated suspension as is obtained in the above preparation process is diluted so that it contains about $1 \times 10^9$/ml of inactivated bacteria, of the composition already stated, in 0.5 ml. A 1% strength solution of human albumin or plasma substitute Haemaccel[R] (manufacturer: Behringwerke AG, 3500 Marburg, Federal Republic of Germany) containing 0.01% of thiomersal in 0.85N NaCl solution is used for the dilution.

2 ml vials are filled under sterile conditions with 0.5 ml of the dilute suspension described above, frozen at about $-45°$ C. and then dried in vacuo in a lyophilization apparatus. The drying temperature should not exceed $+36°$ C. The entire lyophilization process lasts 24 hours. After the lyophilization, the vials are closed with rubber stoppers under a nitrogen atmosphere and are fitted with aluminum caps.

An aqueous aluminum phosphate gel with a concentration of $AlPO_4$ of 2 mg/ml is used to introduce the aluminum phosphate and at the same time as a solvent for redissolving before administration.

The preparation of the aluminum phosphate gel has been described in the preceding preparation process.

The aluminum phosphate gel thus obtained is diluted with saline solution (about 12 times) so that a final concentration of 2 mg/ml is present, before it is introduced into the ampules.

The ampules with a capacity of 1 ml are charged with an amount of 0.5 ml.

To test the storage life of the vaccine, its ability to form antibodies in mice was determined twice, and in particular immediately after the preparation, on Dec. 3, 1981, and two years later, on Dec. 7, 1983. Immunization of the mice:

Six groups of 10 mice each (male, NMRI outbred, weight 16–20 g) were immunized intraperitoneally with the vaccine. Two doses (0.5 ml of the vaccine) were injected at an interval of two weeks. The 20 mice used as the control group, of the same breed and of the same weight, were injected only with aluminum phosphate gel (0.5 ml). Two weeks after the second injection, the blood was removed aseptically and pooled according to groups. After coagulation, the serum from each pool was obtained by centrifugation and was stored deep-frozen at $-22°$ C. until serological testing was carried out.

Preparation of the antigens (agglutinogens)

Nine homologous bacteria strains contained in the vaccine were used for preparation of the antigen; the strain Ec 654 could not be agglutinated (R form) and could not be used as an agglutinogen. The lyophilized cultures of bacteria strans were suspended in 9 ml of nutrient medium (veal infusion broth—Difco) and the culture was incubated at 37° C. for 24 hours. The second subculture was used for the antigen preparation. 600 ml of nutrient medium (veal infusion broth) were inoculated with seed culture (each strain separately). The cultures were incubated at 37° C. for 36 hours. Formalin was then added to a final concentration of 0.1%. The cultures were incubated at 37° C. for 7 days. Each culture was then tested for the absence of live bacteria and for sterility. The inactivated bacteria suspension was centrifuged in a cooled centrifuge (Sorval) at 3,000 rpm for one hour. The sediment was resuspended in phosphate buffer/saline solution (pH 7.2), so that a concentration of about $20 \times 10^9$ bacteria in one milliliter was achieved. About $2 \times 10^9$ bacteria/ml were used as the agglutinogen for the agglutination sample.

Agglutination test

The mouse sera were diluted in 1:2 dilution steps with phosphate-buffered physiological saline solution of pH 7.2. In each case 0.3 ml of serum dilution was mixed with the same volume of antigen in Kahn tubes. One tube without the addition of serum served as the antigen control. After 18 hours at 37° C., and a further 24 hours at 4° C., the reaction was checked. The maximum dilution at which visible agglutination of the bacteria was still detectable was taken as the titer of the particular serum. Negative and positive sera were also run as controls for all the batches.

The following geometric means were found for the agglutinin titers of the mouse sera:

| Antigen | Titer (reciprocal values) | |
|---|---|---|
| | tested in 1981 | tested in 1983 |
| E. coli 455 UB | 1,015.5 | 905.1 |
| E. coli 525 UB | 905.1 | 1,015.5 |
| E. coli 560 UB | 1,015.5 | 1,015 5 |
| E. coli 616 UB | 905.1 | 806.3 |
| E. coli 719 UB | 1,280 | 1,280 |
| Klebsiella pneumoniae 16B | 201.6 | 201.6 |
| Proteus mirabilis 63B | 160.0 | 142.5 |
| Proteus morganii 58B | 113.1 | 113.1 |
| Streptococcus faecalis 676 | 71.3 | 71.3 |

From these results, it can be seen that the vaccine retains its full activity for at least two years when stored at 4° C.

The indications for the vaccine are, in particular, cystitis, prostatitis, cystopyelitis and pyelonephritis.

Patients who do not have an acute fever condition (contraindication) are given a total of 3 intramuscular injections, each containing 0.5 ml of vaccine, at intervals of in each case 1 to 2 weeks. If severe reactions to vaccination occur, the treatment should be discontinued.

One year later, a repeat injection should be administered, also in a dose of 0.5 ml, as a booster.

383 patients with symptomatic, bacteriologically confirmed urinary tract infections in various hospitals have so far been inoculated with the vaccine and then observed further for longer than one year. The results show that the inoculation causes an improvement in the resistance of the urinary tract lasting for at least one year, resulting in substantial protection from recurrent urinary tract infections. The results of the clinical investigations are summarized in the following table.

| | Number of recurrences/reinfections during the observation period of 1 to 12 months | | |
|---|---|---|---|
| | 0 | I | VI |
| Investigator | Start of study | 1 to 2 months | 7 to 12 months |
| Li/BS | 62/62 | 6/62 | — |
| | 100% | 9.3% | |
| Li/SH | 118/118 | 12/113 | 2/115 |
| | 100% | 10.6% | 1.7% |
| Ru/H, DE | 203/203 | 15/183 | 3/194 |
| | 100% | 8.2% | 1.5% |
| Total number vaccinated | 383/383 | 33/358 | 5/309 |
| | 100% | 9.2% | 1.6% |
| Control | 198/198 | 26/148 | 18/146 |
| | 100% | 17.6% | 12.3% |

The tolerance may be described as good. No serious side effects occurred. The vaccine can also be used in pregnancy without problems; experience obtained on more than 100 pregnant women document this.

Finally, essential features and advantages of the invention and also the results of further pharmacological and clinical investigations with the new vaccine, which are not described in detail here, are summarized:

The quantitative composition of the 10 different strains is in accordance with the frequency distribution of the pathogens of urinary tract infections: 75% of the strains are E. coli strains (uniformly represented) and 25% are Proteus mirabilis, Proteus morganii, Klebsiella pneumoniae and Streptococcus faecalis strains.

These uropathogenic strains are inactivated so that they contain the antigens which afford protection, such as, for example, fimbrial antigens and O-antigens. The strains selected as antigens also show, when tested in a protection test on mice, cross-protection against the heterologous strains of the same species of pathogen.

As has been demonstrated with the mouse weight gain test, the inactivated antigens represented in the vaccine became clearly less toxic after storage in a cold-storage room for at least 6 months.

The vaccine induces an immune response in inoculated animals (mice, rabbits) and also in inoculated humans, protects mice from a lethal infection and protects rats from experimental pyelonephritis.

The quantitative and qualitative composition corresponds to the amount of antigens which still induces a good immune response, and results in no serious side effects or no side effects in the patient.

The vaccine also induces secretory immunoglobulin A in the urine of inoculated patients.

The vaccine cures a person suffering from a urinary tract infection; it protects relapsing patients from reinfection for at least 12 months.

The vaccine can be prepared in liquid or lyophilized (freeze-dried) form. In the lyophilized form, an aluminum phosphate gel is used as a solvent for redissolving before administration.

We claim:

1. A vaccine for curative and prophylactic treatment of urinary tract infections in humans, which comprises (1) inactivated bacteria which originate from cultures of 8 to 14 uropathogenic bacteria strains isolated from the urine of a person suffering from an infection of the urinary tract, of the species: Escherichia coli, Klebsiella pneumoniae, Proteus mirabilis, Proteus morganii and Streptococcus faecalis, and are present in an amount of about 50 million to 500 million germs of each strain per ml, one half to three quarters of the strains used belonging to the Escherichia coli species, and (2) aluminum phosphate in colloidal form in an amount of 1.5 to 10 mg of AlPO$_4$ per ml, suspended in a sterile isotonic solution.

2. A vaccine as claimed in claim 1, in which the inactivated bacteria originate from 6 strains of the species Escherichia coli and 1 strain each of the other four abovementioned species.

3. A vaccine as claimed in claim 1, in which the inactivated bacteria originate from the following strains (in-house designation or DSM receipt number): Escherichia coli Ec 455 UB, 525 UB, 560 UB, 616 UB, 654 UB and 719 UB, or DSM 3229 to DSM 3234, Klebsiella pneumoniae 16 B, or DSM 3235, Proteus mirabilis 63 B, or DSM 3238, Proteus morganii 58 B, or DSM 3237, and Streptococcus faecalis 676, or DSM 3236.

4. A vaccine as claimed in claim 1 in which the inactivated bacteria are present in a total amount of about $2\times 10^9$ germs per ml.

5. A vaccine as claimed in claim 1, further comprising a preservative.

6. A process for the preparation of a vaccine as claimed in claim 1, which comprises culturing, by themselves on a suitable nutrient medium, each of the 8 to 14 uropathogenic bacteria strains of the species *Escherichia coli, Klebsiella pneumoniae, Proteus mirabilis, Proteus morganii* and *Streptococcus faecalis,* which have been isolated from the urine of a person suffering from an infection of the urinary tract and of which half to three quarters belong to the species *Escherichia coli,* and, when culturing is concluded, removing the particular biological material formed and inactivating it by known methods, mixing amounts of the inactivated bacteria obtained from the individual strains with one another and diluting the mixture with an amount of a sterile isotonic solution such that about 50 million to 500 million germs of each strain are present per ml, and adding aluminum phosphate in colloidal form up to a concentration of 1.5 to 10 mg of $AlPO_4$ per ml.

7. The process as claimed in claim 6, wherein 6 strains of the species *Escherichia coli* and 1 strain of each of the other four abovementioned species are used for culture.

8. The process as claimed in claim 6, wherein the following strains are used for culture (in-house designation or DSM receipt number): *Escherichia coli* Ec 455 UB, 525 UB, 560 UB, 616 UB, 654 UB and 719 UB, or DSM 3229 to DSM 3234, *Klebsiella pneumoniae* 16 B, or DSM 3235, *Proteus mirabilis* 63 B, or DSM 3238, *Proteus morganii* 58 B, or DSM 3237 and *Streptococcus faecalis* 676, or DSM 3236.

9. The process as claimed in claim 1 wherein the biological material is inactivated by heating an aqueous suspension to 55° to 60° C. for about 1 hour, by treatment with formaldehyde or by irradiation with $\gamma$-rays.

10. The use of a vaccine as claimed in claim 1 for curative or prophylactic treatment of urinary tract infections, which comprises administering the said vaccine intramuscularly in a dose of in each case 0.5 ml three times at intervals of in each case 1 to 2 weeks to a person suffering from an infection of the urinary tract, in the urine of whom the presence of at least one of the following bacteria: *Escherichia coli, Streptococcus faecalis, Proteus* and *Klebsiella pneumoniae,* has been detected, and administering an intramuscular booster dose of 0.5 ml one year later.

11. A vaccine, as in claim 1, which is in the lyophilized form.

12. A vaccine as in claim 5, wherein said preservative comprises o-ethylmercurithio-benzoic acid.

* * * * *